United States Patent [19]
Katinger et al.

[11] Patent Number: 5,942,245
[45] Date of Patent: Aug. 24, 1999

[54] APPLICATION OF SOD IN LIPOSOMES

[75] Inventors: Hermann Katinger; Karola Vorauer-Uhl; Eckhard Fürnschlief, all of Wien, Austria

[73] Assignee: Polymun Scientific Immunbiologische Forschung GmbH, Austria

[21] Appl. No.: 08/836,185

[22] PCT Filed: Nov. 6, 1995

[86] PCT No.: PCT/EP95/04352

§ 371 Date: Jul. 1, 1997

§ 102(e) Date: Jul. 1, 1997

[87] PCT Pub. No.: WO96/14083

PCT Pub. Date: May 17, 1996

[30] Foreign Application Priority Data

Nov. 4, 1994 [EP] European Pat. Off. .............. 94117409

[51] Int. Cl.$^6$ .......................... A61K 9/133; A61K 38/44; C12N 9/02
[52] U.S. Cl. .......................... 424/450; 424/94.4; 435/189
[58] Field of Search .................................. 424/94.4, 450; 435/189

[56] References Cited

U.S. PATENT DOCUMENTS

| | | | |
|---|---|---|---|
| 4,235,871 | 11/1980 | Papahadjopoulos et al. | 424/19 |
| 5,116,616 | 5/1992 | Gonenne | 424/94.4 |
| 5,185,154 | 2/1993 | Lasic et al. | 424/450 |
| 5,618,521 | 4/1997 | De Rigal et al. | 424/59 |
| 5,710,033 | 1/1998 | Hallewell et al. | 435/189 |
| 5,714,143 | 2/1998 | Blake et al. | 424/94.4 |

FOREIGN PATENT DOCUMENTS

| | | |
|---|---|---|
| 0 207 039 A1 | 12/1986 | European Pat. Off. . |
| 0 457 910 A1 | 11/1991 | European Pat. Off. . |
| 63-77824 | 4/1988 | Japan . |
| 1-319427 | 12/1989 | Japan . |
| 5-97694 | 4/1993 | Japan . |
| WO 87/0138 | 3/1987 | WIPO . |

OTHER PUBLICATIONS

C.R. Seances Soc. Biol. Fil., vol. 179, No. 4, 1985, pp. 429–439, A.M. Michelson et al., "La superoxide dismutase et la pathologie des radicaux libres".

Am. Rev. Respir. Dis., vol. 132, No. 1, 1985, pp. 164–167, R.V. Padmanabhan et al., "Protection Against Pulmonary Oxygen Toxicity In Rats By The Intratracheal Administration of Liposome–Encapsulated Superoxide Dismutase or Catalase".

Eur. J. Dermatol., vol. 4, No. 5, 1994, pp. 389–393, A.A. Youssefi et al., "Oxyradical Involvement in PUVA–Induced Skin Reactions. Protection By Local Application of SOD".

Free Radical Biology & Medicine, vol. 16, No. 6, 1994, pp. 821–824, D.B. Jacoby et al., "Influenza Virus Induces Expression of Antioxidant Genes In Human Epithelial Cells".

Drugs Exp. Clin. Res., vol. 17, No. 2, 1991, pp. 127–131, Y. Mizushima et al., "Topical Application of Superoxide Dismutase Cream".

Bull. Cancer, vol. 80, No. 9, 1993, pp. 799–807, J.L. Lefaix et al., "La Fibrose Cutanéo–Musculaire Radio–Induite (III): Efficacité Thérapeutique Majeure De La Superoxyde Dismutase Cu/Zn liposomiale".

Am. Rev. Respir. Dis., vol. 131, No. 4, 1985, pp. 633–637, R.J. McDonald et al., "Effect of Superoxide Dismutase Encapsulated In Liposomes or Conjugated with Polyethylene Glycol on Neutrophil Bactericidal Activity in vitro and Bacterial Clearance in vivo".

Dermatologica, vol. 179, Supplement No. 1, 1989, pp. 101–106, Yukie Niwa, "Lipid Peroxides and Superoxide Dismutase (SOD) Induction in Skin Inflammatory Diseases, and Treatment with SOD Preparations".

Delanian et al., Radiother. Oncol. 32:12–20, Aug. 1994.

Nakae et al., Am. J. Pathol. 136:787–795, Apr. 1990.

Schaechter et al. (eds), Mechanisms of Microbial Disease, Williams & Wilkins, Baltimore, MD, pp. 408–415, 1989.

*Primary Examiner*—Rebecca E. Prouty
*Attorney, Agent, or Firm*—Oliff & Berridge, PLC

[57] ABSTRACT

Superoxide dismutase (SOD), preferably rhSOD, is used in liposomes, optionally mixed with hyaluronic acid and/or at least one physiologically acceptable carrier, and other optional additives, to prepare a pharmaceutical composition useful against increased concentrations of superoxide radicals and/or the damage caused thereby. These compositions can be administered topically, orally and/or parenterally to prevent and/or heal burns, skin lesions due to radiation, inflammations, rheumatic and arthritic diseases, bronchitis, ARDS, emphysema, allergic oedemas and other inflammatory process, possibly trigged by microbial infections. They may also be used in the cosmetic treatment of furuncles, acne and the like. They may also be used to improve the preservability of organic, preferably biogenic, materials, in particular organ transplants and liquids with organic components, as well as foodstuffs.

20 Claims, No Drawings

APPLICATION OF SOD IN LIPOSOMES

BACKGROUND OF THE INVENTION

1. Field of the Invention

The present invention relates to the use of superoxide dismutase (SOD), preferably of recombinant human SOD, in liposomes, for the preparation of pharmaceutical compositions, optionally mixed with hyaluronic acid and/or at least one physiologically acceptable carrier and/or other optional additives, for therapeutic and/or prophylactic use against increased concentrations of superoxide radicals and/or damage caused thereby.

2. Discussion of Related Art

Superoxide radicals are extremely reactive intermediate forms of the natural oxygen molecule and, as a result of this property, can irreversibly damage organic compounds in the cells of the human body. As protection from the dangerous effect of these superoxide radicals, the cells have an enzyme which is capable of rapidly converting such superoxide radicals into the more rapidly metabolizable and less toxic hydrogen peroxide ($H_2O_2$).

$$2[O_2]^- + 2H + \xrightarrow{SOD} H_2O_2 + O_2 \quad (I)$$

Thereafter, the hydrogen peroxide, which is still toxic, is usually decomposed by the enzyme catalase into the harmless components water and oxygen.

$$2H_2O_2 \xrightarrow{Catalase} 2H_2O + O_2 \quad (II)$$

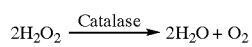

The enzyme superoxide dismutase (SOD) occurs both in the human and animal body and in plants and presumably in all microorganisms which come directly into contact with atmospheric oxygen (aerobic bacteria and fungi). In the cells of higher organisms (eucaryotes), there are mainly two types of this SOD: a manganese-containing SOD which is localized in the mitochondria and is very similar to the bacterial SOD, and a second one which is present freely in the cytosol and contains copper and zinc atoms.

Unless stated otherwise, the term SOD is to be understood below as meaning mainly Cu,Zn—SOD, except for that from bovine blood erythrocytes, and bacterial or mitochondrial Mn—SOD and/or Fe—SOD, and recombinant human Cu,Zn—SOD (rhSOD).

Superoxide dismutase has been known under the name Orgotein since 1939, but the dismutase activity was not discovered and described until 1969, by McCord and Fridovich. Its practical use was limited in the past in particular by the short life or short biological availability of the protein under natural conditions, which of course has an adverse effect on the frequency of the dosage intervals, the therapeutic doses to be chosen and the associated costs.

The most investigated and used SOD to date was the Cu,Zn—SOD from bovine blood erythrocytes. Following severe and in some cases even fatal adverse reactions in the clinical-therapeutic use of bovine blood SOD, especially against arthritic diseases, preparations containing bovine blood SOD were prohibited, for example, in Austria. In particular, the preparation of recombinant human SOD, as described, for example, in AT 397 812 (Polymun Scientific, 1994), offers a way out of this situation.

Inter alia, the incorporation of SOD molecules in liposomes is a possible method for controlling the short life or short biological availability of the active substance SOD (Senga et al. 1990, Transplant. Proc. 22:2025).

The very first trial applications related to the treatment of inflammations and inflammatory processes of the skin. However, uses in osteoarthritis and rheumatic arthritis are now also reported in the literature (Hartmann et al. 1986, Proc. Natl. Acad. Sci. U.S.A. 83:7142; Bannister et al. 1987, Critical Rev. Biochem. 22:111). Especially in the area of medicine, it is also reported that SOD improves the storability of organs for the purpose of a subsequent transplantation (Olson et al. 1988, Transplant. Proc. 20:961), and a use for food preservation has already been mentioned (WO 85/01503).

SUMMARY OF THE INVENTION

The primary object of the present invention is to provide pharmaceutical compositions for transporting SOD, preferably rhSOD enclosed in protective liposomes, in a gentle, effective manner and with better bioavailability, to those parts of the body which are to be treated. In spite of a continuing general prejudice on the part of those skilled in the art, the inventors have been able in particular to use liposomally packaged SOD successfully for burns and scalds and for radiation damage, caused, for example, by UV radiation or ionizing radiation, in particular by external application. In the case of exposure to radiation, prophylactic use, for example together with a radiation-filtering or radiation-absorbing screening agent, is also possible in addition to therapeutic use.

A further object is to provide a pharmaceutical composition based on SOD in liposomes, which overcomes the stated disadvantages of the prior art and thus opens up additional fields of use, in particular in the area of cosmetics.

It is a further object of the present invention to transport SOD, preferably rhSOD enclosed in protective liposomes, in a gentle, effective manner and with better stability and a longer lasting effect, to the organic materials to be treated, for example vegetable or animal tissues, organs, organ or tissue transplants, cosmetic preparations based on organic substances and/or foods.

A particular object of the present invention is the use of the synergistic effect of a mixture of hyaluronic acid and SOD. Hyaluronic acid has also recently become known to those skilled in the art for its "free radical acceptor properties", and its use in wound treatment has repeatedly been described (Amgen, NO 9214480, 1992). The use of hyaluronic acid together with Colony Stimulating Factor (CSF) or Platelet Derived Growth Factor (PDGF) for accelerating wound healing has also been described in the literature (Zymogenetics, U.S. Pat. No. 5,128,321, 1992), and hyaluronic acid has also been described as an additive in cosmetics and pharmaceutical preparations (Shiseido, WO 9104279, 1991).

On the other hand—surprisingly—a combination of hyaluronic acid and SOD, in particular a mixture of hyaluronic acid and liposomally incorporated SOD, has not been described to date. To what extent this represents or represented a prejudice on the part of those skilled in the art cannot be adequately assessed at the present time. In any case, it was surprisingly found, in the course of the experiments which have finally led to the present invention, that hyaluronic acid supports and reinforces the effect of SOD, also of liposomally incorporated SOD, in an almost ideal manner.

DETAIL DESCRIPTION OF PREFERRED EMBODIMENTS

Burns and scalds and/or a harmful dose of ionizing or UV radiation induces, inter alia, a reaction which takes place in a cascade-like manner and is responsible, for example, for the "after-burning" (=increase in necrotic damage) in the 2nd and especially 3rd dimension. The problem with the conventional first aid for burn wounds and radiation damage in practice is that, apart from immediate treatment with cold water, there has to date been no locally applicable agent which could be used as first aid for suppressing after-burning phenomena. Fat-containing or fat-free burn ointments or gels are not known to have any advantageous, healing effect in this direction, nor is such an effect to be expected.

It is therefore more than surprising that SOD in liposomes has been used neither in animal medicine nor in human medicine for the local, external first aid of wounds, except in the form of injections directly into the wound, especially as SOD in liposomes has been known for more than 5 years (J03101626, 1989).

However, the literature also states that the use of SOD for supporting wound healing or the survival of Balb/c mice with burns and artificially produced infection was unable to achieve any significant success in healing (Fang et al., The Journal of Trauma, Vol. 30, No. 4: 453–456, 1990).

In spite of these disadvantages of the prior art and the possible prejudice on the part of those skilled in the art against liposomally provided active substances for topical, in particular external, application to the body or to the body surface, the inventors, thanks to their inventive assumptions, have unexpectedly been able to use SOD in liposomes successfully against thermal and radiation-induced skin and tissue damage.

The following considerations played a role here: as a result of the trauma itself, also in the case of intense sunburn, the barrier of the corneum disappears for the most part or even completely, i.e. there was an opportunity for the active substance to display its effect optimally in the direction of the corium and subcutaneously under the corium, particularly in the case of early application of SOD, preferably rhSOD, in liposomes, before the development of an oedema.

The surprising success in external topical treatment of the stated tissue damage is presumably furthermore due to the fact that the tissue injury results in increased formation of macrophages which, in the course of their immunological protective function (defence against infection, elimination of cell fragments), come into contact with the liposomes, break up their lipid layer and thus liberate the content—the SOD molecules—whereupon these in turn can display their superoxide-degrading and hence also tissue-protecting activity.

In the course of the experiments which have finally led to the present invention, it was also surprisingly found that, thanks to the inclusion of the SOD molecules in liposomes, not only was their stability and bioavailability increased but also the concentration of SOD required to achieve the desired effect could be reduced by a factor of 10 compared with SOD compositions without liposomes, without having to accept lower activity. Moreover, because of the liposomal dosage form, a physiologically more advantageous dosage of the active substance at the place of demand is also achieved, which of course has a very advantageous effect on the amount and/or frequency of the doses and the associated costs. This advantageous effect of the physiologically more advantageous dosage of liposomally incorporated SOD on site also plays a role in inflammations and inflammatory processes at the body surface and in the interior of the body and in processes for improving the stability of organic materials.

It is however also presumed that the direct enzymatic action of the SOD protein may not be the only decisive factor for the success of healing. It is known that other enzymes, e.g. cytochrome A, histone, lysozyme and ribonuclease, for example in dimerized form, have additional properties which considerably extend those of the monomer, the action spectrum and the respective field of use of the dimeric proteins thus being advantageously extended in comparison with the monomers (Bartholeyns and Zenebergh, Europ. J. Cancer, Vol. 15, 1979, 85–91).

In the course of enclosing the SOD in the liposomes according to the invention, as described, for example, in Example 1, at least a part of the SOD molecules having a molecular weight of about 32000 Dalton agglomerate to give aggregates of 2 or 3 molecules. Although it has not yet been demonstrated, it is possible that these aggregates result in an additional advantageous effect, for example with regard to increased stimulation of phagocytosis activities.

With the use of hyaluronic acid mixed with SOD, in particular rhSOD, with or without liposomes, it has surprisingly been found that a synergistic effect occurs in so far as, particularly in the case of external application, substantially smoother and more elastic new tissue forms in comparison with an SOD-treated burn wound without hyaluronic acid. This effect was also found in the case of inflamed wounds on the body surface. Hyaluronic acid mixed with liposomal SOD serves both as a synergistic free radical acceptor and as a pharmaceutically acceptable carrier.

In the experiments on which the present invention is based, it was also unexpectedly found that, with the use of a composition of hyaluronic acid mixed with SOD, in particular rhSOD in liposomes, a synergistic effect is obtained in so far as a significantly longer stability or duration of action of the composition itself in comparison with the SOD treatment without hyaluronic acid, and hence also a longer stability of the treated materials, result; this effect is evident in particular when the SOD is present freely in the composition, i.e. not enclosed in liposomes. Both SOD alone and hyaluronic acid alone were substantially inferior in this effect to a mixture of the two components.

This synergistic effect of a mixture of SOD and hyaluronic acid is possibly promoted because the hyaluronic acid both protects the phospholipid layers of the liposomes and/or the sensitive SOD molecules from harmful, i.e. mainly oxidizing, influences from the outside and, after deactivation of the SOD, also makes its own, although only small, contribution to the elimination of superoxide radicals.

The present invention includes several different embodiments of the use of SOD, in particular rhSOD in liposomes, with or without hyaluronic acid and optionally in combination with carriers and/or further additives, for the preparation of pharmaceutical compositions against a number of indications.

One embodiment or one feature of the invention relates to the use of SOD, in particular of recombinant human SOD (rhSOD) in liposomes, optionally mixed with hyaluronic acid and/or a physiological acceptable carrier and optionally further additives usually used for pharmaceutical formulations, for the preparation of pharmaceutical compositions against burns, scalds and radiation damage, in particular that caused by UV radiation.

In an embodiment according to the invention, for example, rhSOD incorporated in liposomes is formulated as a germ-free wound gel, the optionally admixed carrier being low-fat or fat-free and originating from the group consisting of the organic and inorganic hydrogels, and is applied directly to the burn wound. In addition to clinical use for patients with second and third degree burns, for example from accidents, such a formulation is also particularly useful for persons who have suffered extensive or localized sunburns during sunbathing by water or in the snow.

Particularly in the case of burn wounds, it has also proven particularly advantageous if the SOD-containing liposomes are applied to the injured areas in liquid form by spraying on from a spray can or spray bottle. This avoids direct contact of the wound with the fingers or another aid for application, for example of a gel, and thus reduces the danger of an additional infection.

In another embodiment, liposomally incorporated SOD, optionally with hyaluronic acid and/or further additives, is applied to—preferably—sterile wound plaster and/or wound dressings, in order thus to have a rapidly available and easily handled material for the effective treatment and/or self-treatment of small and medium-sized burn wounds or skin burns at the place of occurrence. The particular advantage of this application form is the simple manner of application, as it can also be carried out safely by medically untrained persons, for example by parents whose child has burnt its finger on the cooker or has scalded itself with hot water.

A particular aspect of the present invention is the use of SOD, in particular rhSOD in liposomes, for the preparation of compositions which are used before, during or after exposure to radiation. For purely therapeutical applications, i.e. after excessive exposure to radiation, for example in the case of sunburn, it is advisable, in order to reduce the consequences of the exposure to radiation, to use the SOD compositions according to the invention, preferably rhSOD in liposomes, optionally mixed with at least one physiologically acceptable carrier and/or hyaluronic acid, and optionally further additives, in the form of emulsions, suspensions, solutions, lotions or at least low-viscosity ointments or gels.

Compositions which can be applied to the damaged skin areas by means of an atomizing apparatus, for example a spray, are particularly advantageous. On the one hand, this avoids direct contact and hence possible infection of the injured skin with possibly dirty fingers or other aids for application of the composition and, on the other hand, a more or less painful application by rubbing, for example of a relatively highly viscous gel, is thus dispensed with.

For the prophylactic and simultaneously therapeutic use before and during exposure to radiation, particularly suitable compositions according to the invention are those which, in addition to SOD and optionally hyaluronic acid, also contain at least one radiation-filtering or radiation-absorbing protective agent, preferably a light filter or UV absorber, in particular a UVB filter. Further substances, especially skin care factors, may also be present.

As a result of the presence of SOD and optionally of hyaluronic acid in addition to conventional light filter substances, the unpleasant consequences of a sunburn can be considerably reduced. Such prophylactic and therapeutic sunscreen preparations can advantageously be used for any kind of sunbathing, whether on the beach, on the mountains, at sea, on the ski slope or in a solarium. In particular people with sensitive skin and those skin types which are not tanned by UV radiation benefit most from this application form of the present invention.

Another embodiment relates to the preparation of compositions for therapeutic and/or prophylactic use in the case of acute and chronic inflammations and inflammatory processes, rheumatic diseases, in particular rheumatic joint inflammations and/or osteoarthritis, as well as inflammations of the respiratory tract, in particular bronchitis, acute respiratory distress syndrome (ARDS), emphysema and other inflammatory processes. Promising possibilities are thus opened up especially for the area of cosmetic applications for prophylactic and/or therapeutic treatment of local inflammations of the skin, such as, for example, furuncles or acne, which are known to constitute a considerable cosmetic impairment for many people.

In one embodiment according to the invention, for example, rhSOD incorporated in liposomes is formulated as sterile wound gel, the optionally admixed carrier being low-fat or fat-free and originating from the group consisting of the organic and inorganic hydrogels, and is applied directly to the inflamed area. A low-fat or fat-free carrier is advantageous in particular for open, inflamed wounds, since increased lipid concentrations in the wound area may lead to the formation of toxic degradation products. Hyaluronic acid can be particularly advantageously used in such compositions, either as the only carrier or mixed with at least one further carrier of the above category. Moreover, further suitable additives, as are usual, for example, for pharmaceutical formulations, may also be present in the compositions according to the invention.

Particularly in the case of surface inflammations, it has also proven particularly advantageous if the SOD-containing liposomes are applied to the inflamed area by spraying on from a spray can, spray bottle or other spray apparatus. This avoids direct contact of the wound with the fingers or with another aid for application of the composition and thus reduces the danger of an additional infection. In certain cases, however, it may also be advantageous if at least one of the compositions according to the invention is applied on—optionally sterile—wound dressings, for example wound coverings, sticking plaster and the like. Wound dressings prepared in this manner are suitable for simple and rapid treatment, optionally also self-treatment, for example in the case of inflamed wounds and/or rheumatic joint inflammations.

In a further embodiment of the present invention, liposomally incorporated SOD, in particular rhSOD, together with hyaluronic acid and optionally at least one additional low-fat or fat-free carrier, in particular from the group consisting of the organic and inorganic hydrogels, and optionally further additives, is formulated as an injection solution and successfully used for rheumatological and/or orthopaedic indications, for example rheumatic joint inflammations or osteoarthritis.

Injection may be given both directly into the affected joints (intraarticularly) or body regions or in another parenteral, preferably intravenous, manner.

To a certain extent, rheumatic-arthritic symptoms can also be relieved by external treatment, for example by an external application, also according to the invention, of SOD in liposomes, in particular mixed with hyaluronic acid. The active substances can be formulated and used here both in the form of ointments or gels, if necessary mixed with additional, preferably low-fat or fat-free, carriers, in particular from the group consisting of the organic and inorganic hydrogels, and in the form of sprays or tinctures. Suitable additives, as usually used for pharmaceutical formulations, may also be present in the compositions. In some cases, an accompanying, oral administration of liposomal SOD in the form of tablets, capsules, sugar-coated tablets, powders, etc. may also have a supporting effect.

In a further embodiment, certain degenerative phenomena, such as emphysema, in particular cutaneous emphysema, could be successfully reduced and suppressed by the use, according to the invention, of SOD in liposomes, optionally mixed with hyaluronic acid and/or at least one physiologically acceptable carrier. Here too, additional, phagocytosis-stimulating effects of the SOD aggregates in the liposomes may play a synergistic role, in addition to the purely enzymatic action of the SOD.

The same is also likely to be the case for the successful therapeutic use of the pharmaceutical compositions of the present invention in the case of inflammations of the respiratory tract and of the lungs, such as, for example, bronchitis, acute respiratory distress syndrome (ARDS) and pulmonary emphysema. In this case, particularly the application of a solution or emulsion of liposomally incorporated SOD by inhalation has proven particularly suitable.

The use of the liposomal SOD composition is very successful particularly in the area of cosmetic disorders. Small local inflammations, furuncles, acne and similar phenomena can be effectively treated by the use, according to the invention, of the SOD-containing compositions, in particular in the form of ointments, gels or creams or in liquid form by spraying on. In the case of repeated, preferably regular, application, a certain prophylactic effect with respect to the formation of new skin inflammation, for example of furuncles, can also be achieved. This too may be associated with an activation of phagocytosis processes which is triggered or stimulated by the SOD aggregates.

With the use of a mixture of liposomal SOD and hyaluronic acid, moreover, the healing of the inflammation(s) is achieved with formation of new, more elastic and especially smoother tissue in comparison with hyaluronic acid-free compositions. This is a considerable advantage especially for cosmetic applications on visible parts of the body, for example on the face.

The compositions, according to the invention, of the present invention are most effective when, depending on the use and method of application, the SOD is present in a concentration of $\geq 0.01\%$ by weight, in particular of 0.01 to 5% by weight, and the optionally additionally present hyaluronic acid in an amount of $\geq 0.05\%$, in particular 0.1 to 5% by weight, based on the prepared, ready-to-use composition. For topical applications, an amount of 0.01 to 1 mg SOD/$cm^2$ lesion area or body surface area has proven most suitable. On the other hand, oral or parenteral applications are advantageously carried out with SOD doses of 0.5 to 50 mg/kg body weight, the dose advantageously being adjusted to 0.5 to 10 mg/kg·day for repeated SOD doses during a therapy.

The present invention furthermore relates to the use of SOD for the preparation of compositions which can be used for improving the stability of various organic, preferably biogenic, materials, and to processes for improving the stability of such organic materials by the use of the compositions according to the invention.

In principle, SOD, preferably rhSOD in liposomes, in the form of an aqueous solution or emulsion with or without hyaluronic acid can be formulated according to the present invention and used directly for a preservative application. In various cases, however, the admixture of one or more suitable carrier substances and/or further additives usually used for pharmaceutical compositions may be advantageous, for example for permitting or simplifying a certain, desired application form.

However, what is important for the use, according to the invention, of the compositions, for example in a process for improving the stability of the organic materials according to the present invention, is that the organic material is brought at least partially into contact with at least one of the compositions described here.

In an embodiment of the present invention, liposomally incorporated SOD, in particularly rhSOD, is initially taken in a suitable buffer solution in order to preserve organs or organic tissues which were removed from a donor for the purpose of transplantation, in the period between removal and reimplantation. A composition having an SOD content of 0.1–1% by weight has proven useful here. The organ- or tissue-preserving treatment is best carried out by first irrigating the relevant organ by conventional methods of organ preservation, in particular by injection or infusion of the liquid composition into the organ, for example a heart, a kidney, a liver, etc., and preferably then by immersing or preferably placing the respective organ or tissue part in a bath which also contains liposomal SOD either in the same buffer or in another suitable buffer. This makes it possible on the one hand considerably to extend the period of temporary storage and on the other hand to reduce possible organ or tissue damage after reimplantation.

Gratifyingly, it has been found that an additional synergistic effect of the type described above could be achieved in this case by mixing hyaluronic acid, for example in concentrations of about 0.05–2.5% by weight, with the existing emulsion of liposomal SOD and buffer.

In another embodiment, liposomal SOD in a liquid composition—with and without hyaluronic acid—is applied to foods, for example by means of spray bottles, spray cans or other spray apparatuses. In particular, highly perishable meat products as well as dairy products of all kinds and fruit and vegetables could be decisively improved in their stability by means of these simple measures which can easily be applied. The liposomally packaged SOD acts as a sort of antioxidant in this case.

Immersion baths which contain at least one of the compositions according to the invention and in which the organic materials, for example various foods, are immersed or placed over a desired period are also suitable for bringing the active substances SOD and optionally hyaluronic acid into contact with the organic material.

A further embodiment of the present invention relates to the use of free SOD, in particular rhSOD, or liposomal SOD, mixed with hyaluronic acid and optionally at least one further suitable carrier, for improving the stability of cosmetic preparations based on organic substances, in particular of skin care agents. Experiments have shown that both SOD in liposomes alone and free or liposomally incorporated SOD mixed with hyaluronic acid are very suitable for improving the stability of the organic material in cosmetic preparations, such as ointments, creams, gels, lotions, waters, milks and the like when added to the latter. Particularly in the case of the mixture with hyaluronic acid, an additional positive effect is obtained with regard to a certain increase in the suppleness and smoothing of the skin after application of cosmetics improved in this manner.

The concentration of SOD in this application is preferably between 0.1 and 5% by weight, whereas the amount of optionally present hyaluronic acid is most preferably chosen as 0.5–5% by weight, based on the final composition. If moreover one or more carrier substances are to be admixed, they should preferably be low-fat or fat-free and optionally originate from the group consisting of the organic and inorganic hydrogels.

SOD concentrations of from 0.1 to 100 mg/kg of organic material have proven useful for improving the stability of organic materials, such as, for example, vegetable and animal tissues, organ transplants, foods, in particular highly perishable meat and sausage products, or cosmetics based on organic substances.

In order further to explain the potential applications according to the invention and the mode of action of the compositions described herein, some Examples are given below. The Examples serve for better understanding and are in no way intended to limit the content or scope of the present invention.

EXAMPLE 1

Use for Scalds 70 albino rabbits were divided into 7 groups (A–G). An area of 5×10 cm on the back of each rabbit was shaved. After deep anaesthesization, the shaved back area of each individual rabbit was dipped for exactly 16 seconds into a tray having an opening of exactly 3×5 cm and filled with hot water at 93.5–95° C. This resulted in second to third degree scalds. The scalded areas were treated according to Table 1 below and immediately covered with sterile wound dressing with an aluminium inlay. The dressing was changed daily.

The liposomes with incorporated rhSOD were prepared as follows: the injection method according to Batzri and Korn (Batzri, S. Korn, E. D., 1973, Biochim. Biophys. Acta 298:1015–19) was used as the preparation method for the largely multilaminar liposomes. The lipid components L-a-phosphatidylcholine, dipalmitoyl (DPPC) cholesterol and stearylamine are dissolved in 96% ethanol in a molar ratio of 7:1:2. The lipid concentration of the liposome solution is 10 $\mu$mol/ml. The ethanol volume is chosen so that the ethanol concentration in the preparation is less than 7%. The lyophilized rhSOD is dissolved in PBS. The protein concentration of the aqueous phase is 10 mg/ml. Both solutions are thermostated at 37° C. The liposomes are produced by continuous injection of the ethanolic phase into the aqueous phase. To separate off the unincorporated rhSOD or the ethanol, the liposome solution is subject to diafiltration against PBS (ultra/diafiltration unit from Amicon; membrane; YM 100).

For the final formulation, the carbogel (Carbopol®, highly acidic acrylic acid polymers having a high molecular weight, DAB9) is rehydrated in distilled water and the pH is adjusted to 7.5. The liposome solution and the rehydrated gel are homogeneously mixed and stored at 4° C. The entire preparation process is carried out using sterile solutions and in laminar flow conditions (sterile clean-room bench).

Preparation of the liposomally incorporated rhSOD-hyaluronic acid gel: Lyophilized hyaluronic acid is rehydrated in the aqueous liposome solution, and the prepared gel is stored at 4° C.

The above-mentioned experimental animals were examined continuously by a veterinarian, and no signs of a clinical disease in the animals were found during the course of the experiment. The animals also showed no posttraumatic pain symptoms after waking from the anaesthesia, but posttraumatic analgesia was initiated as a precaution.

Group F remained untreated as the control group. The remaining groups were treated according to the following scheme:

TABLE 1

| Test group | Number of animals | Identification numbers | Dose and administration |
|---|---|---|---|
| A | 10 | 1–10 | 0.1 mg of rhSOD/cm$^2$ of the lesion, in liposomes; applied 2 × on the first day |
| B | 10 | 11–20 | 1 mg of rhSOD/cm$^2$ of the lesion, in gel without liposomes; applied 1 × on the first day |
| C | 10 | 21–30 | 1 mg of rhSOD/cm$^2$ of the lesion; injected intralesionally |
| D | 10 | 31–40 | Control group: gel with empty liposomes; applied 1 × on the first day |
| E | 10 | 41–50 | Control group: gel without liposomes; applied 1 × on the first day |
| F | 10 | 51–80 | Control group: no treatment |
| G | 10 | 61–70 | 0.1 mg of rhSOD in liposomes/cm$^2$ of the lesion, with hyaluronic acid; applied 2 × on the first day |

The size of the wounds (planimetry, photographic documentation), the local status (colour, presence of necroses, signs of epithelization, contractures, hair, cutimetry, granulation tissue), histopathological skin examinations and, macroscopically, the general course of healing (photographic documentation) were evaluated statistically.

For the parameters investigated, a positive effect of the rhSOD incorporated in liposomes on the healing regeneration processes in the treated experimental animals was found. The effect of the rhSOD 24 hours after production of the lesion was most clear. Thus, for example, there was a significant difference in lesion size between the test groups, the transition zone of the necrosis into the surrounding unscalded skin being substantially less affected by the scald in the rhSOD-treated animals. Histological examinations, too, confirmed the macroscopic results. The most advantageous histopathological picture was found for test groups A and G. Histologically, test groups A and G were the only ones of all test groups to show no residual necroses after 4 weeks. The overall findings for groups A and G gave the following picture:

the lesion size was unchanged in comparison with the other test groups after 24 hours;

the width of the oedema on the other hand was substantially reduced and aggression was accelerated;

there were no residual necroses in the corium;

test group G moreover exhibited the formation of smoother and more elastic new tissue compared with all other test groups.

In an observation period of 24 hours, the positive effect of the rhSOD incorporated in liposomes could be clearly demonstrated although the dose of the rhSOD in test groups A and G was ten times lower than in test groups B and C. The after-burning phenomena of the scald wounds and in particular the oedema declined fastest and most substantially in the groups treated with liposomally incorporated rhSOD.

EXAMPLE 2

Use for Burns

An experiment with the production of burn wounds was carried out analogously to the method of M. Choi and H. G.

Ehrlich (American Journal of Pathology 142, 1993, 519–529). 40 rats (Wistar, male rats) of 300–350 g body weight were kept under standard conditions. Burn wounds in the form of a strip pattern were made on the anaesthesized rats (anaesthetic: pentobarbital, i.p.) with a stamp which was heated in boiling water. For this purpose, the stamp was pressed for 30 seconds against the shaved skin of the animals. In order to obtain the desired pattern on the skin, the stamp according to Choi and Ehrlich (1993) had a comb-like design.

The rats were divided into 4 groups of 10 animals each (Table 2).

TABLE 2

| Test group | Number of animals | Administration |
|---|---|---|
| 1 | 10 | Control group: no treatment |
| 2 | 10 | Carrier gel with empty liposomes |
| 3 | 10 | Gel with rhSOD in liposomes |
| 4 | 10 | rhSOD in liposomes with hyaluronic acid in carrier gel |

The preparation of the liposomes and of the gels was carried out analogously to Example 1. The rats were treated six times at regular intervals in the course of 48 hours, the first treatment being carried out a few minutes after production of the lesion. Liposomally packaged rhSOD was used in an amount of 0.05 mg/cm$^2$ of the lesion, and the amount of hyaluronic acid in the composition used was 3% by weight.

The planimetry and the macromorphology of the wound pattern which is brought about by the design of the stamp were used as an evaluation criterion for the potential action. Furthermore, standard histology (haematoxylin, eosin and vital staining; according to H. Millesi, 1970, Chirurgia Plastica et Reconstructia Vol. 8, Springer Verlag Berlin, Heidelberg, New York) of the tissue samples was carried out. Samples were taken after 0 h, 25 h, 72 h, 7 days and 21 days.

In groups 3 and 4, the pattern produced by the stamp shape was retained, i.e. the burned strips remained vital. In groups 1 and 2, on the other hand, confluence to a more or less uniform wound surface occurred. In groups 3 and 4, an advantageous histopathological picture was also observed. In the groups treated with rhSOD incorporated in liposomes, the pattern of the unexposed strips was maintained. The surfaces affected by the stamp pressure were replaced by granulation and scar tissue, the majority of which was necrosis-free. In groups 1 and 2, a uniform scar surface without a pattern and with some deep necroses was observable.

EXAMPLE 3

Use for Radiation Damage

Hairless mice were exposed to the minimum erythema dose (MED) of UV radiation. The experimental setup was as described by B. C. Pence and M. F. Naylor (B. C. Pence, M. F. Naylor 1993, J. of Investigative Dermatology 95: 213–16). A single dose of UVB radiation (290–320 nm) from a Westinghouse FS-40 sun lamp was used in such a way that the mice were exposed to a total energy of 0.09 J/cm$^2$. This dose corresponds to three times the MED for Caucasian volunteers. 40 mice in 4 groups of 10 animals each were used (Table 3).

TABLE 3

| Test group | Number of animals | Administration |
|---|---|---|
| 1 | 10 | Control group: no treatment |
| 2 | 10 | Carrier gel with empty liposomes |
| 3 | 10 | Gel with rhSOD in liposomes |
| 4 | 10 | rhSOD in liposomes with hyaluronic acid in carrier gel |

The liposomes and gels were prepared analogously to Example 1. The gel was applied immediately (2–3 min) after exposure to radiation and then twice more at regular intervals of 4 hours. The gel in the composition used contained 0.5% by weight of hyaluronic acid, and the administered dose of rhSOD was 0.5 mg/cm$^2$ of irradiated body surface. A visual colour comparison of all animals at regular time intervals was carried out as an evaluation criterion. Furthermore, the occurrence of "sunburn cells" was tested.

In groups 3 and 4, a significantly lower erythema in comparison with groups 1 and 2 occurred after 10 hours. After 24 hours, tissue samples were taken and were tested for the characteristic "sunburn cells". In groups 3 and 4, no "sunburn cells" or only isolated "sunburn cells" occurred. The intensity of redness could be correlated with the occurrence of sunburn cells.

EXAMPLE 4

Comparison of Different Application Forms 140 male OF1 (outbred) mice (from the Institute for Experimental Animal Breeding and Keeping, Himberg, Austria), all between 8 and 10 weeks old, were divided into 14 groups (A–N) according to the randomization principle. Under ether anaesthesia, the mice were inoculated intranasally with 50 µl of PBS solution which contained 1×10$^5$ PFU/mouse (=2–2.5×LD$_{50}$) of the influenza virus A/WSN/33 (referred to below as WSN). The treatment of the WSN-infected mice began on the 4th day after infection, i.e. at the beginning of the occurrence of clinical symptoms of the influenza disease in the mice. The mice were treated once daily up to day 11 after the infection. They were treated topically, subcutaneously, intravenously and intranasally with preparations which contained rhSOD in the following liposomal vesicle types:

a) rhSOD in small, unilamellar vesicles (SUV), size≦about 100 nm, b) rhSOD in injection vesicles (IV), diameter≦about 200 nm, and c) rhSOD in multilamellar vesicles (MLV), diameter<about 500 nm.

Table 4 shows the experimental setup and the results obtained. For the topical treatment, a liposomal rhSOD gel was applied to the ventral side of the mice, especially in the breast region, by rubbing in once per day. A skin area of about 10 cm$^2$ was thus covered with an approximately 2 mm thick gel layer. The concentrations stated in Table 4 relate to the treated area in cm$^2$. The intranasal application of rhSOD took place with the animals under ether anaesthesia. 0.05 ml of a suspension containing rhSOD in IV (1 mg/ml) was introduced into the nostrils of the mice by means of a micropipette. An injection was given into the caudal vein for intravenous administration of the rhSOD suspensions (cf. Table 4), while the same suspensions as for the i.v. injection were injected subcutaneously into the neck and/or shoulder region for the subcutaneous application. The number of deaths among the mice did not increase after the 15th day after the infection (period tested: day 15 to day 25 after the infection), so that mice which have survived on the 15th day were regarded as having been cured of the influenza infection.

The pathogenesis of an influenza virus infection in mice tends to indicate a hyperreaction of the immune defence of the host organism as a direct effect in relation to the multiplication of the virus. The formation of free oxygen radicals in the course of an influenza infection is influenced by the massive infiltration of lymphoid cells into the lung tissue and by increased xanthine oxidase activity in the lungs and in the serum of the mice (Oda et al., Science, 1989, 244 (4907): 974-6).

| Group | Application form and dose | Survivors per 10 mice |
|---|---|---|
| A | Topical application of a gel of rhSOD incorporated in SUV; dose: 0.15 mg rhSOD/cm² treated surface | 4 out of 10 |
| B | Topical application of a gel of rhSOD incorporated in IV; dose: 0.15 mg rhSOD/cm² treated surface | 4 out of 10 |
| C | Topical application of a gel of rhSOD incorporated in MLV; dose: 0.42 mg rhSOD/cm² treated surface | 3 out of 10 |
| D | Topical application of a gel with IV without rhSOD | 2 out of 10 |
| E | s.c. application of a suspension of SOD incorporated in SUV Dose: 0.5 ml; suspension: 1 mg rhSOD/ml | 8 out of 10 |
| F | s.c. application of a suspension of rhSOD incorporated in IV Dose: 0.5 ml; suspension: 1 mg rhSOD/ml | 8 out of 10 |
| G | s.c. application of a suspension of rhSOD incorporated in MLV Dose: 0.5 ml; suspension: 3 mg rhSOD/ml | 5 out of 10 |
| H | s.c. application of 0.5 ml of an IV suspension without rhSOD | 1 out of 10 |
| I | i.v. application of a suspension of rhSOD incorporated in SUV Dose: 0.5 ml; suspension: 1 mg rhSOD/ml | 9 out of 10 |
| J | i.v. application of a suspension of rhSOD incorporated in IV Dose: 0.5 ml; suspension: 1 mg rhSOD/ml | 10 out of 10 |
| K | application of a suspension of rhSOD incorporated in MLV Dose: 0.5 ml; suspension: 3 mg rhSOD/ml | 4 out of 10 |
| L | i.v. application of 0.5 ml of an IV suspension without rhSOD | 1 out of 10 |
| M | i.n. application of a suspension of rhSOD incorporated in IV Dose: 0.05 ml; suspension: 1 mg rhSOD/ml | 8 out of 10 |
| N | Control group without treatment | 1 out of 10 |

Result

Mice which were treated parenterally (s.c., i.v. and i.n.) with rhSOD in SWV or IV liposomes survived in most cases (groups E, F, I, J, M) in comparison with the control groups which were either not treated at all or treated only with liposomes without SOD (groups H, L and N). It was also found, surprisingly, that mice which were treated with rhSOD in MLV were less well protected against the fatal influenza infection although in these liposomes preparations a larger amount of rhSOD was used (groups C, G and K). The reason for this is probably the vesicle size (in the region of 500 nm; for comparison: IV≦about 200 nm; SUV≦about 100 nm), poorer distribution and a lower degree of fusibility of the MLV with the cells, as was established on the basis of an in vitro fusion assay (fusion assay: CHO cells were incubated overnight with 20 μmol of rhSOD-containing IV and MLV liposomes, and rhSOD was detected by immunofluorescence after treatment with 1% Triton X100).

The topical treatment of the influenza-infected mice with rhSOD gel resulted in only partial protection against the fatal consequences of the disease; nevertheless, this protection was significant in the groups which were treated with SUV or IV preparations (group A and B). The results show that free oxygen radicals play an important role with regard to the fatal effects of the influenza infection in mice and that rhSOD, incorporated in small liposomal vesicles (SUV and IV), has a considerable therapeutic potential with respect to this viral infection.

The results also show that rhSOD, incorporated in small liposomes (SUV, IV) having a diameter of about 200 nm or less, evidently can overcome the skin barriers even in the case of essentially healthy, intact skin and can penetrate into relatively deep tissue layers in order to display its protective action against the viral infection in the lung region (pneumonia). Liposomally incorporated rhSOD can therefore be used not only for i.v., s.c. and i.n. applications but also in the form of ointments, gels, creams or other suitable formulations, optionally in combination with other active substances and/or including further additives, as an effective therapeutic agent for the treatment of diseases which are associated with free oxygen radicals, for example of—optionally microbial—inflammations, in particular of the upper respiratory tract and of the lung.

EXAMPLE 5

Topical Application in the Case of Herpes labialis

In a human experiment, rhSOD, incorporated in small, unilamellar vesicles (SUV) having a vesicle diameter of about 100 nm or less, was tested against a local skin inflammation in the mouth area caused by fever blisters on the lip (herpes labialis). Herpes infections and herpes diseases are known to be difficult to treat and in general very unpleasant for the persons affected, that is to say frequently cause pain (e.g. in the case of herpes zoster), itching, burning, weeping and/or cosmetically disadvantageous effects, especially in the face area.

The liposomal rhSOD preparation based on Carbopols gel had a consistency similar to that of a skin cream and was applied in a concentration of about 0.15 mg of rhSOD per cm² of treated area, once or twice per day, directly to the inflamed area. Noticeable relief was observed within a few hours after only the first application, and the typical symptoms had very largely died away after treatment for only 3 days.

EXAMPLE 6

Topical Application Against Allergy

The same rhSOD preparation as in Example 5 was tested in another human experiment against allergic reactions. The allergy symptoms were red eyes and swellings around the eyes and in the region of the eyes and nose, possibly as additional effects of an existing hay fever allergy. In addition to the unpleasant facial tensions caused by the swelling and the psychological suffering additionally associated with this, impairment of normal vision was also present.

The rhSOD gel was applied, analogously to Example 5, in a concentration of about 0.15 mg of rhSOD per cm$^2$ of treated area in the entire affected facial area, in the same way as a skin cream. The result was impressive: after only a single application, the swellings disappeared almost completely; as a precaution, cream was applied a second time on the following day, but a further treatment was no longer necessary. The symptoms had virtually completely disappeared.

EXAMPLE 7

Use Against Psoriasis

In a further experiment, the rhSOD gel from Example 5 was used to treat psoriasis in a child. The preparation was applied twice a day (in the morning and in the evening), analogously to Example 5, in a concentration of about 0.15 mg of rhSOD per cm$^2$ of treated area, to all affected parts of the body, in the same way as the skin cream.

Result

After treatment for three days, a substantial decline in the reddening of the skin in the region of the inflammation centre and a reduction in itching were observed. This gratifying finding shows that, with external topical application, rhSOD in liposomes can also be used successfully in psoriasis patients, at least to relieve the symptoms—even if not to cure the disease.

What we claim is:

1. A pharmaceutical composition comprising a low-fat or fat free carrier together with recombinant human Cu, Zn—SOD (rhSOD) in unilamellar liposomes having an average diameter of 200 nm or less, wherein the rhSOD is present in a concentration of 0.01 to 5% by weight based on the composition, for topical administration to a human body or part thereof.

2. The method according to claim 1, wherein said condition is due to or associated with an increased level of superoxide radicals.

3. The composition according to claim 1, in combination with hyaluronic acid.

4. The composition according to claim 3, wherein the hyaluronic acid is present in a concentration of from 0.05 to 5% by weight based on the composition.

5. The composition according to claim 1, wherein the low-fat or fat free carrier is selected from the group consisting of organic and inorganic hydrogels.

6. A method for the prophylactic or therapeutic intervention of a pathological condition affecting a human body or part thereof, wherein said condition is susceptible to administration of superoxide dismutase, the method comprising topically administering to the human body or part thereof a pharmaceutical composition comprising a low-fat or fat free carrier together with recombinant human Cu, Zn—SOD (rhSOD) in unilamellar liposomes having an average diameter of 200 nm or less in an amount effective for penetrating from the outside into deeper lying tissue layers of the body or part thereof, to prevent or relieve said pathological condition.

7. The method according to claim 6, wherein said pathological condition affects a human tissue or organ for reimplantation and the composition is externally applied to said tissue or organ before reimplantation.

8. The method according to claim 6, wherein the composition is administered to a substantially healthy area of the skin of the human body for penetrating into adjacent tissue layers in need of such treatment.

9. A method according to claim 6, wherein the pharmaceutical composition further comprises hyaluronic acid.

10. A method according to claim 6, wherein said condition is selected from the group consisting of radiation damage to the skin and adjacent tissues, burns, scalds, inflammatory processes or rheumatic-arthritic diseases.

11. A method according to claim 10, wherein said inflammatory processes are selected from the group consisting of rheumatic joint inflammations, inflammations due to influenza virus or herpes virus infection, skin emphysemas, furuncles, or acne.

12. A method according to claim 6, wherein said condition is selected from the group consisting of redness of the skin, swelling of the skin, and psoriasis.

13. A method according to claim 6, wherein the pharmaceutical composition further contains at least one radiation-filtering or radiation-absorbing screen agent.

14. A method according to claim 13, wherein the at least one radiation-filtering or radiation-absorbing screen agent is a UVB filter.

15. A method according to claim 6, wherein the pharmaceutical composition is administered in the forms of emulsions, suspensions, solutions, lotions, ointments or gels, or by spraying from a spray apparatus.

16. A method according to claim 6, wherein the pharmaceutical composition is administered externally in an amount such that the rhSOD is applied in a dose of 0.01–1 mg/cm$^2$ of treated surface.

17. A method according to claim 6, wherein the pharmaceutical composition is administered in an amount such that the rhSOD is supplied in a dose of 0.5–50 mg/kg body weight.

18. A method according to claim 6, wherein the low-fat or fat-free carrier is selected from the group consisting of organic and inorganic hydrogels.

19. A method according to claim 6, wherein the rhSOD is present in the pharmaceutical composition in a concentration of 0.01 to 5% by weight based on the composition.

20. A method according to claim 9, wherein the hyaluronic acid in the pharmaceutical composition is present in a concentration of from 0.05 to 5% by weight based on the composition.

* * * * *